United States Patent
Picard (10) Patent No.: US 6,692,447 B1
(45) Date of Patent: Feb. 17, 2004

(54) OPTIMIZING ALIGNMENT OF AN APPENDICULAR

(76) Inventor: Frederic Picard, 18 Rue du Champ Gauthier, Barbizon (FR), 77630

( * ) Notice: Subject to any disclaimer, the term of this patent is extended or adjusted under 35 U.S.C. 154(b) by 0 days.

(21) Appl. No.: 09/936,585

(22) PCT Filed: Feb. 7, 2000

(86) PCT No.: PCT/US00/03171

§ 371 (c)(1),
(2), (4) Date: Sep. 13, 2001

(87) PCT Pub. No.: WO00/48507

PCT Pub. Date: Aug. 24, 2000

Related U.S. Application Data (60) Provisional application No. 60/120,706, filed on Feb. 16, 1999.

(51) Int. Cl.[7] .......................... A61B 5/103; A61B 5/117
(52) U.S. Cl. ........................................ 600/587; 600/595
(58) Field of Search ................................ 600/407, 425, 600/426, 587, 595; 602/1; 606/102

(56) References Cited

U.S. PATENT DOCUMENTS

| | | | |
|---|---|---|---|
| 4,631,676 A | 12/1986 | Pugh | |
| 4,649,934 A | 3/1987 | Fraser et al. | |
| 4,813,436 A | 3/1989 | Au | |
| 5,099,859 A | * 3/1992 | Bell | 128/781 |
| 5,249,581 A | 10/1993 | Horbal et al. | |
| 5,368,030 A | 11/1994 | Zinreich et al. | |
| 5,394,457 A | 2/1995 | Leibinger et al. | |
| 5,402,800 A | 4/1995 | Hollis | |
| 5,514,143 A | 5/1996 | Bonutti et al. | |
| 5,551,429 A | 9/1996 | Fitzpatrick et al. | |
| 5,611,353 A | 3/1997 | Dance et al. | |
| 5,649,928 A | 7/1997 | Grundei | |
| 5,748,767 A | 5/1998 | Raab | |
| 5,776,143 A | 7/1998 | Adams | |
| 5,779,710 A | 7/1998 | Matsen, III | |
| 5,823,958 A | 10/1998 | Truppe | |
| 5,846,245 A | 12/1998 | McCarthy et al. | |
| 5,848,967 A | 12/1998 | Cosman | |

FOREIGN PATENT DOCUMENTS

| | | | | |
|---|---|---|---|---|
| WO | WO 97/23172 | * | 7/1997 | ........... A61B/19/00 |
| WO | WO 98/06346 A1 | | 2/1998 | |
| WO | WO 98/35625 A1 | | 8/1998 | |
| WO | WO 98/40037 A1 | | 9/1998 | |
| WO | WO 98/41152 A1 | | 9/1998 | |

OTHER PUBLICATIONS

Leitner et al., Computer–Assisted Knee Surgical Total Replacement, Lecture Notes in Computer Science, Mar. 1997, pp. 630–638, Published by Springer.

* cited by examiner

Primary Examiner—Max F. Hindenburg
Assistant Examiner—Jonathan Foreman
(74) Attorney, Agent, or Firm—Gardner Carton & Douglas LLP (57) ABSTRACT

A system for determining pivot centers for proximal and intermediary articulations of an appendicular skeleton. The system includes a single marker affixed to a bone, the marker having a signal transmitter; a sequence involving at least one movement for moving a portion of the appendicular skeleton; a signal receiver for collecting data points correlating to the position and orientation of the marker; at least one processing device for selecting a number of skeletal positions during the sequence using the collected data points; and for assigning a value to each posture representing the position and orientation of the marker in a predetermined point of reference, and an algorithm for determining the coordinates of the rotational centers of the proximal and intermediary articulations using the assigned values.

22 Claims, 4 Drawing Sheets

OPTIMIZING ALIGNMENT OF AN APPENDICULAR

RELATED APPLICATIONS

This Application claims priority to U.S. Provisional Application No. 60/120,706, filed Feb. 16, 1999, which is incorporated herein by reference.

FIELD OF THE INVENTION

The present invention concerns a process for determining the pivot center of proximal and intermediary articulations, also known as joints, of an appendicular skeleton.

BACKGROUND OF THE INVENTION

The appendicular skeleton comprises arms and legs and includes the proximal articulations of those limbs (i.e., hips and shoulders) and the intermediary articulations (i.e., elbows or knees) and distal articulations (wrists or ankles). The articulations are connected by proximal bone segments (humerus for arms or femur for legs) and distal bone segments (radius for arms or tibia for legs).

It is common for appendicular joints to be replaced with prosthetic devices. During such replacements, it is very important that the joint be properly aligned—a misaligned bone can shorten the lifespan of the replacement joint considerably, for example, as much as by 20% to 50% of the time. Proper alignment using traditional methods requires a significant amount of skill and experience.

During a surgery involving part of the appendicular skeleton, it is important for proper alignment to know the pivot centers of the proximal and intermediary articulations of the skeleton. In fact, when it is necessary to cut the proximal bone segment, for instance, it is important to make the cut exactly at a right angle with respect to the plane connecting these two articulations, or pivot centers. It is also useful to optimize pivot centers of articulations for physical therapy applications, and for sports medicine applications. Determining the pivot point can also be used as a diagnostic tool for tracking the progression of certain bone diseases.

In the case of the hip, for instance, the pivot center corresponds to the articulation center of the hip, which is spherical. This is not the case with a non-spherical articulation, such as, for example, the knee. The pivot center of the knee, for instance, corresponds to the average of a range of points (the "cloud point") formed by the pivot centers of this non-spherical articulation during the relative movement of the bone segments surrounding it.

Initially, articulations were positioned by observation. This method resulted in a relatively high failure rate, leading to the development of .mechanically assisted methods, such as those reported in the prior art, such as, for instance, the method disclosed by F. Leitner, F. Picard, R. Minfelde et al., *Computer-Assisted Surgical Total Replacement of the Knee* (published in the Proceedings of the First Joint Conference, Computer Vision, Virtual Reality and Robotics in Medicine, Medical Robotics and Computer Assisted Surgery (1997); and as published by S. L. Delp, et al., *Computer Assisted Knee Replacement*, Clinical Orthopedics and Related Research, 354, 49–56 (1998). Throughout these methods, a set of data are generated which, when analyzed, provides assistance in locating the ideal pivot point. Prior art techniques for generating data include preoperative imagery, where the pivot point is determined prior to surgery. This method, however, is somewhat complicated and requires sophisticated imaging equipment and technicians, and sometimes engineers. In general, traditional techniques used to generate these data remain somewhat rudimentary, and inaccuracies in these data generation techniques create inaccuracies in the pivot points generated even by computer-assisted techniques.

One improvement to traditional pre-surgical determinations of the pivot point utilizes at least four individual markers (optical-type, super-resonant, magnetic or inertial) which are surgically screwed into the bones, and each of which each is associated to a means of detection, such as a camera connected to a computer. This allows the medical staff to monitor the positioning and orientation of each marker in real time during a surgical procedure. For purposes of this invention, positioning is the x, y and z cartesian coordinates of the marker, and orientation is the polar coordinates of this marker, expressed at the point of reference point.

A When using this prior art method on a leg, for instance, the first two markers are affixed on either side of the knee, at the extremities toward the tibia and the femur. Two additional markers are affixed on the pelvis and a foot bone, respectively. The patient is placed horizontally, with his femur raised and restrained from movement, and then the tibia is moved toward the motionless femur. A computer is used during this movement to determine the maximal invariancy point, which corresponds to the pivot center of the knee articulation. The pivot center of the hip articulation may be determined in the same manner by moving the femur toward the trunk, and the pivot center of the ankle articulation by moving the foot toward the tibia This solution has certain drawbacks. It requires a large number of markers, and since each marker must be attached to the corresponding bone, it is necessary to affix with screws at least some of these markers to the bone in question. These affixing procedures are time-consuming and can be rather traumatizing for the patient. Also, many methods of moving the body to collect data points for determining the pivot point are used, with differing outcomes. Lastly, differences in bone structure between patients make standardization of traditional techniques for locating optimal pivot points difficult.

Thus, it would be useful to have an optimized positioning method for use with computer assisted orthopedic surgery, which would provide accurately and reliably provide data for generating an optimal articulation pivot point, and which would be faster and less traumatizing for the patient than traditional methods of determining an optimal pivot point. It would also be advantageous to develop a standard technique which could be used for any bone structure and which could account for a wide variety of bone deformities.

The present invention overcomes these drawbacks, in that it provides a means for determining the pivot center of an articulation using only a single marker.

SUMMARY OF THE INVENTION

It is an object of the present invention to provide a method for optimizing the alignment of orthopedic prosthetic devices.

It is a further object of the invention to provide a method of generating data points from physical movements for use in determining the optimal pivot point of a bone articulation that is more accurate and reproduceable than prior art methods.

It is yet another object of the invention to provide a method for determining an optimal pivot point that is fast and less traumatic to the patient as compared to prior art methods.

It is another object of the invention to provide an optimal movement sequence for generating data points which can be used to reliably and accurately locate optimal pivot points of articulations.

It is also an object of the invention to locate an optimal pivot point using a single marker.

In this regard, the invention is a method for determining pivot centers for the proximal and intermediary articulations of an appendicular skeleton, for use during computer-assisted orthopedic surgery or other diagnostic or rehabilitative treatments. The novel method of the invention requires the affixation of a single marker to the bone, which may be affixed by screws or by less traumatic methods such as but not limited to external affixation devices such as elastic bands. Pivot centers for proximal and intermediary articulations may be determined through the use of at least one marker placed between intermediary and distal joints, and pivot centers for intermediary and distal articulations may be determined through the use of at least one marker placed over or at least near the distal joint.

Once the marker is affixed to the bone, the pivot center is determined using rotational movements of the appendicular skeleton in accordance with the sequence of the invention. The sequence of the invention utilizes at least the first and second rotations of the proximal bone segment around the proximal articulation in accordance with the first and second axes, sensibly orthogonal to each other, and at least the third and fourth rotations of the distal bone segment around the intermediary articulation, along the third and fourth axes, sensibly orthogonal to each other.

During the movement sequence, data points on the position and orientation of the marker are collected on a continuous basis from a predetermined point of reference, the localizer. Next, from among the resulting data collected on a continuous basis, a minimal number of distinct postures of the skeleton during the movement sequence are selected, and to each posture is ascribed a value representing the position and orientation of the marker in the predetermined point of reference. Next, from all of the values the coordinates of the optimal pivot point. (also called rotational center) of the proximal and intermediary articulations is determined. Once the optimal pivot points are determined, the optimal alignment of the articulations are possible. "Patient" as used herein denotes legged mammals, most particularly people although it is contemplated and within the scope of the present invention that the methods disclosed herein would work with other legged mammals as well.

BRIEF DESCRIPTION OF THE DRAWINGS

The invention shall be described below with reference to the attached drawings, provided solely as non-limited examples, in which.

DESCRIPTION OF THE INVENTION

Figure 1:
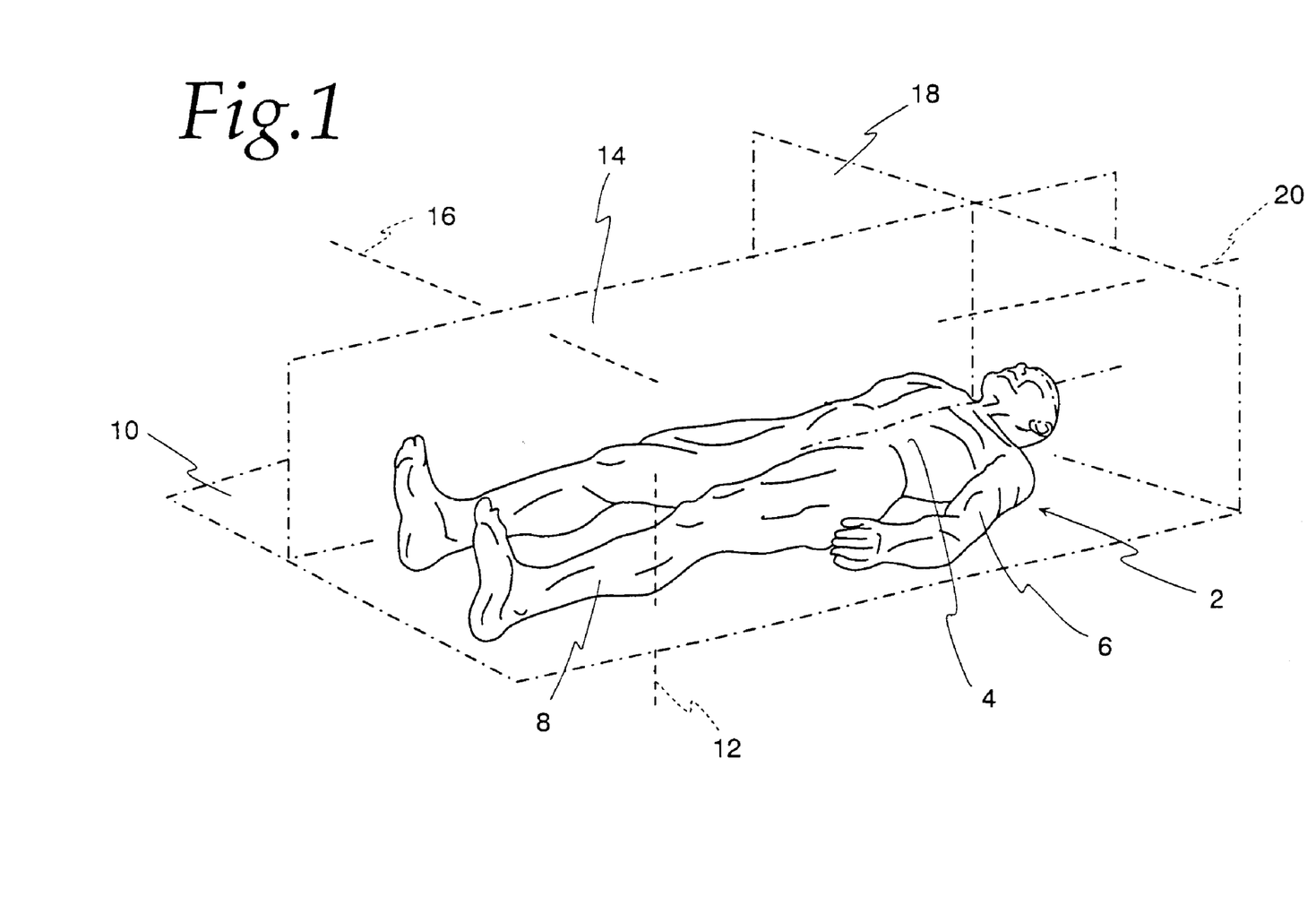
FIG. 1 is a perspective view diagram of a patient in a supine position, showing three planes and three physiological axes connected to the patient.

FIG. 1 represents, in a simplified drawing, a patient lying down, with a complete designation in reference 2. This patient has a trunk 4, two upper appendicular skeletons 6 and two lower appendicular skeletons 8.

The position of a patient is defined by three physiological planes, with three corresponding physiological axes. The frontal plane, designated by reference 10, is associated a beam of frontal axes 12 which are perpendicular to the frontal plane 10 and which therefore extend from the rear to the front of the patient.

The sagittal plane 14 is the median plane of the patient, extending from the medial axis to the lateral side of the patient. A beam of sagittal axes 16, perpendicular to sagittal plane 14, are associated with the sagittal plane.

Axial plane 18 is the horizontal plane perpendicular to the frontal plane 10 as well as the sagittal plane 14, that is going through the cranium of the patient. A beam of axes, called axial 20, is associated with the axial plane 18, and perpendicular to it.

Figure 2:
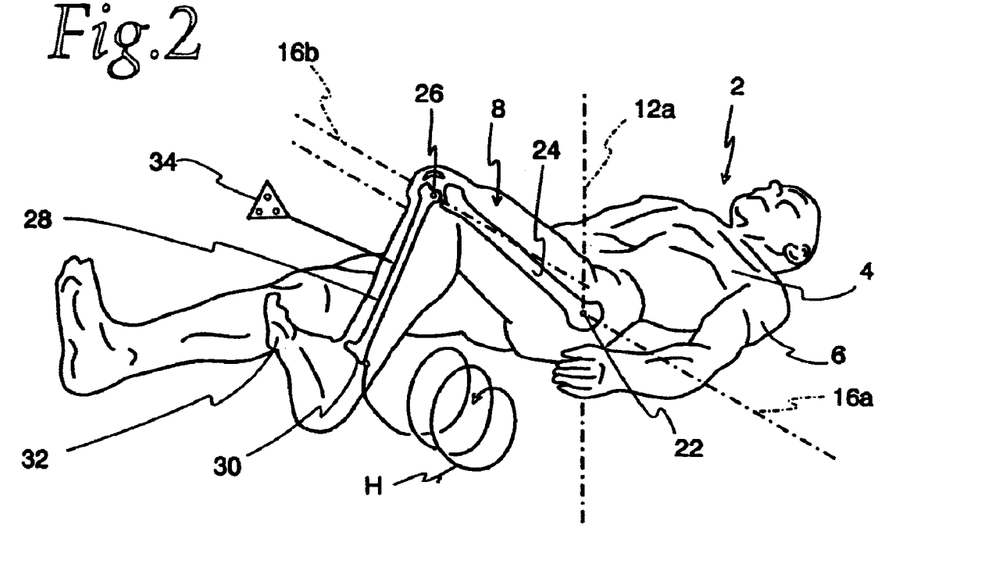
FIG. 2 is a side perspective view showing a patient whose appendicular skeleton is undergoing a first movement from a sequence of the procedure in accordance with the invention.
Figure 3:
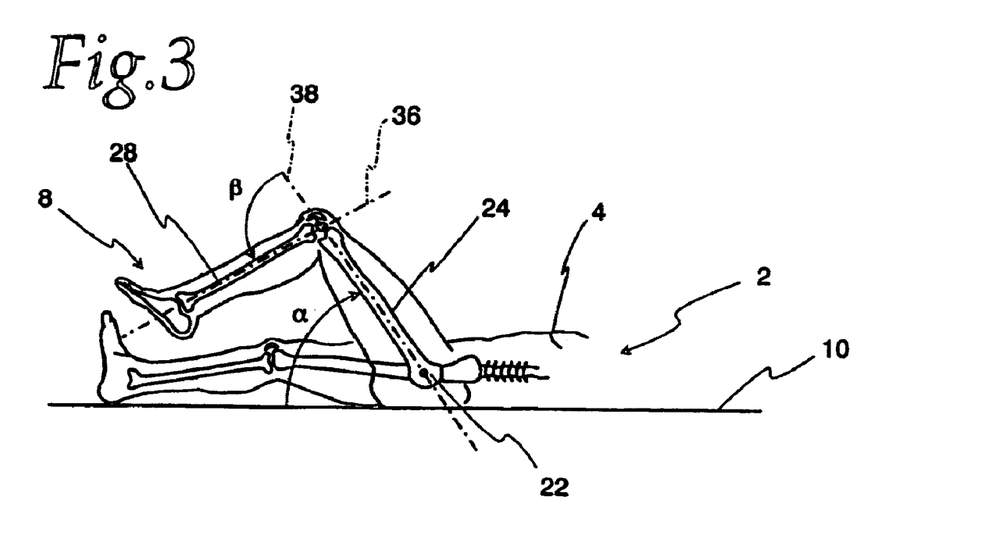
FIGS. 3 is a side perspective view of the appendicular skeleton of a patient that is undergoing a first movement from a sequence of the procedure in accordance with the invention.
Figure 4:
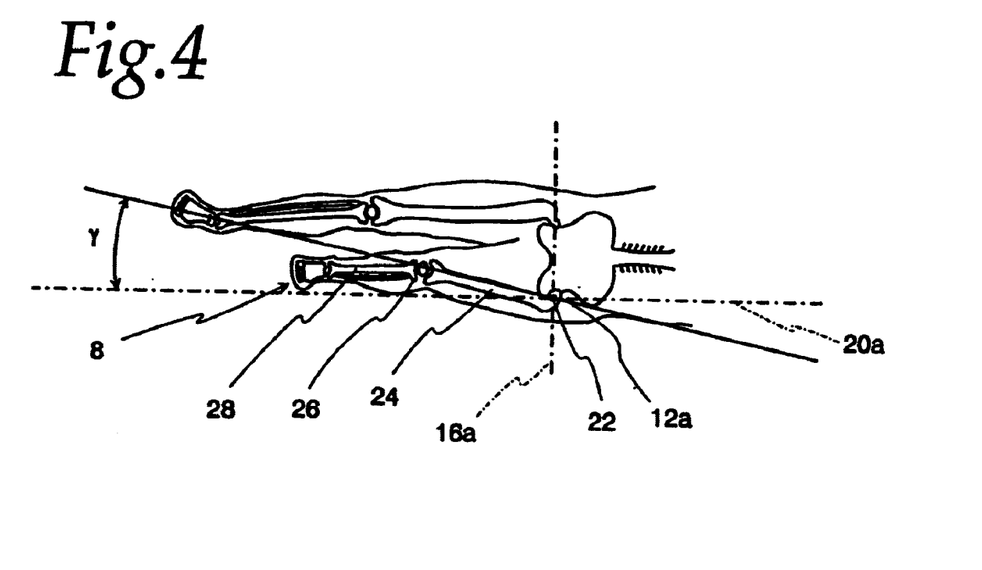
FIG. 4 is a top perspective view of the appendicular skeleton of a patient that is undergoing a first movement from a sequence of the procedure in accordance with the invention.

FIGS. 2 to 4 show the patient in FIG. 1 undergoing a first movement in the determination procedure described herein, in accordance with the methods of the invention.

The lower appendicular skeleton 8 of the patient 2 includes a proximal articulation 22, i.e. the articulation of the hip connecting skeleton 8 to trunk 4, a proximal bone segment 24, i.e. femur, and intermediary articulation 26, i.e. the knee and a distal bone segment 28, i.e. tibia, articulated on the femur 24, by the knee 26. The distal segment 28 ends with a distal articulation 30, i.e. the ankle to which the foot 32 is connected.

The procedure in accordance with the invention simultaneously determines the pivot center of multiple articulations in an appendicular skeleton, such as, for instance, the hip 22 and knee 26 articulations. The preferred embodiment illustrated here will be the hip and knee, although the principles of the invention apply similarly to any set of articulations within the appendicular skeleton, such as but not limited to the articulations of the arm, and the knee-shoulder articulations; Each of these other articulations are also embodiments of the invention and the same principles are used to describe these embodiments as set forth below.

In the illustrated preferred embodiment, hip and knee articulations, an optical marker 34 is placed preferably on the patient's tibia 28. In all embodiments, it is preferable that the marker be placed between an intermediary articulation and a distal articulation. The invention provides an advantage over the prior art in that markers may be affixed without the use of screws, although traditional methods of using screws to affix markers to the bone may be used. Using the method of the invention, markers may be affixed to a bone, such as a tibia, with glue or an elastic band, or any other suitable means that now exists or may be developed. The marker can be affixed anywhere along the bone, in the case of the illustrated embodiment, the tibia 28, and is most optimally located where the bone is very near to the skin of the limb.

Figure 6:
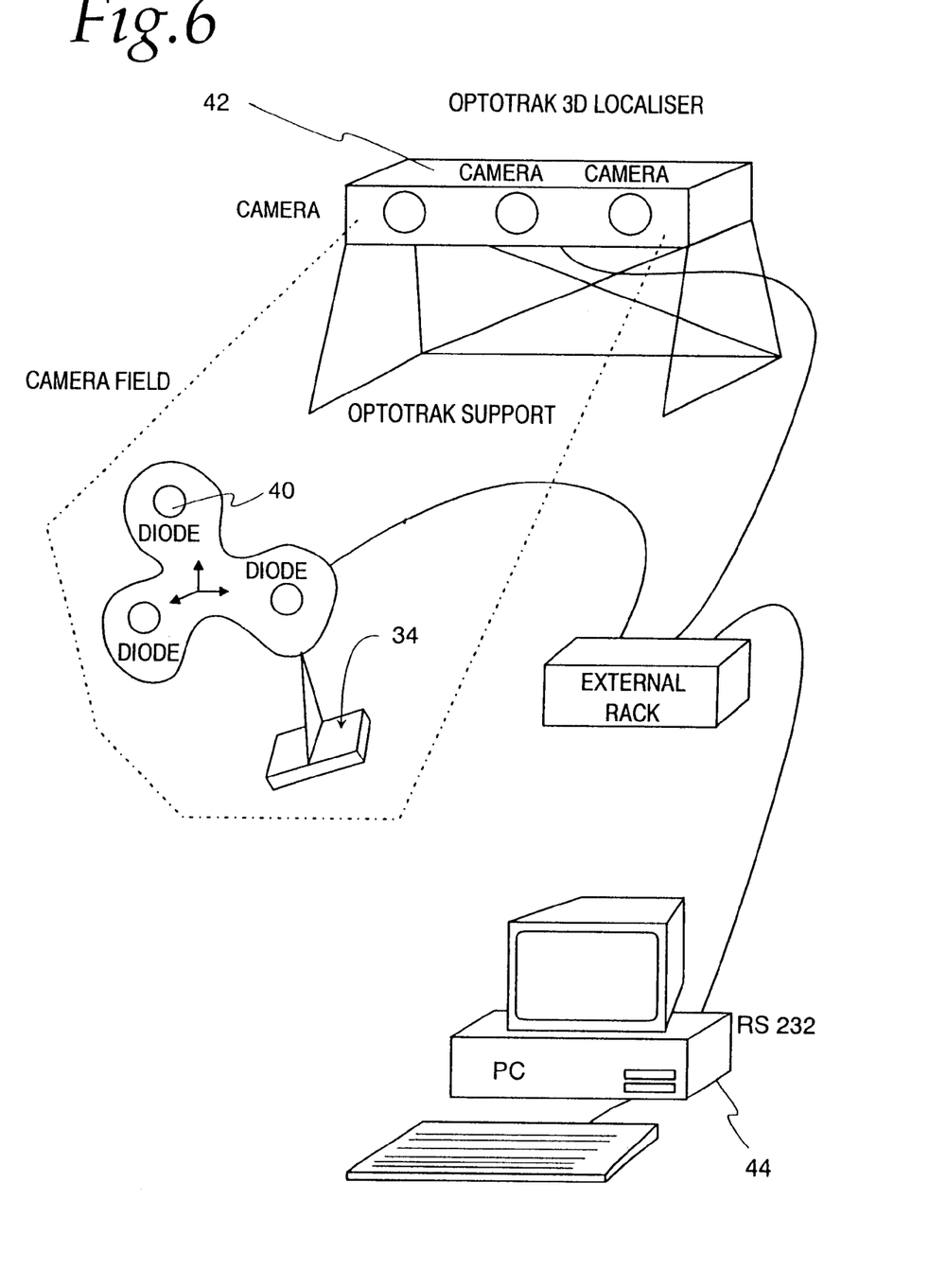
FIG. 6 is a schematic representation of the hardware required for determining the optimal pivot point of an articulation in accordance with the method of the invention.

The marker 34 includes transmitters 40, in this embodiment most optimally at least three transmitters, connected to a receiver, or locator 42 (such as but not limited to a camera), in contact with a processing device 44 such as but not limited to a computer, as shown in FIG. 6. The transmitters 40 may be infrared diodes, for example, or any other marker material suitable for use with the invention, including but not limited to ultrasound or accelerometer markers, and the receivers 42 are adapted to receive signals from the transmitters 40. The marker 34, locator 42, and processing device 44 may be any commercially available system, such as that marketed by the company NORTHERN DIGITAL under the trademark OPTOTRAK, as illustrated in FIG. 6. The receiver insures the locating, on a continuous basis, of the position and orientation of the marker at the point of reference of this receiver. The computer connected to the locator allows measurement and data collection of distinct values indicative of the positions and orientations of the marker.

The starting position of the first movement to which patient 2 is subjected to determines the pivot center of the hip 22 and knee 26 articulations, as illustrated in FIGS. 3 and 4. In this position, seen from the side (FIG. 3), the patient's trunk 4 is horizontal, the femur is raised at an angle $\alpha$ of about 60° from the axial axis 20a going from the articulation of the hip 22. The main axis 36 of the tibia 28 is inclined with regard to the main axis 38 of the femur 24, at an angle $\beta$ of about 90° in that resting position. Moreover, given the above (FIG. 4), the femur 24 forms an angle $\gamma$ with regard to axis 20a of about −10°.

The first movement of the sequence in accordance with the invention requires a moving, such as but not limited to a pedaling, of the appendicular skeleton 8 combined with a rotation of the skeleton around the axial axis and plane 20a going through the articulation of the hip 22. The articulation of the ankle 30, therefore, is subjected to a movement in the shape of an H helix.

During the pedaling movement, angle $\alpha$ varies alternatingly between around 40° and 60°, angle $\beta$ varies alternately between around 20° and 120°, while angle y increases continuously from about −10° to 20°. The diameter D of the helix along which the ankle 30 moves is about 30 cm. During this movement, the number of revolutions of the helix is between about 5 and 50, although fewer or more revolutions may be used.

This first movement described with references in FIGS. 2 to 4 prompts three rotations, i.e. a rotation of the femur 24 around the frontal axis and plane 12a going through the hip 22, a rotation of this femur around the sagittal axis and plane 16a going through the hip 22, as well as a rotation of the tibia around the sagittal axis and plane 16b going through the articulation of the knee 26.

During this movement, the locator enables finding the position and orientation of the marker. We select distinct postures through the computer, i.e. 150 in the example in question. This selection is run at regular time periods during this movement. Six values are designated for each posture, i.e. three Cartesian coordinates and three polar coordinates of the marker for the point of reference determined by the locator. This first movement, therefore, results in 900 data points obtained.

Figure 5:
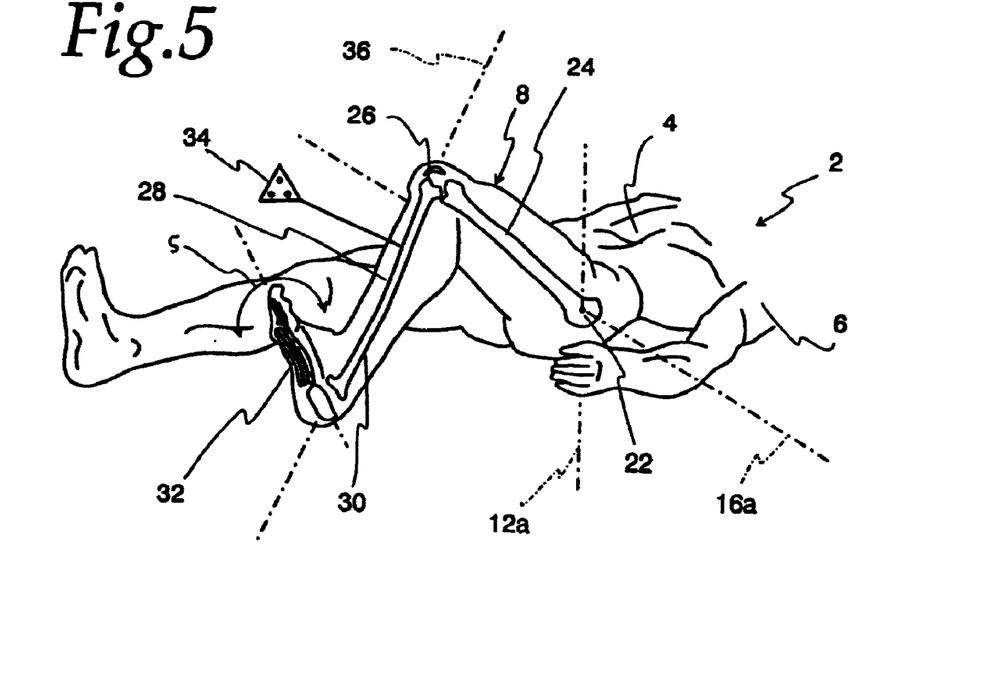
FIG. 5 is a side perspective view showing a patient whose appendicular skeleton is undergoing a second movement from a sequence of the procedure in accordance with the invention.

The sequence in accordance with the invention includes a second movement shown in FIG. 5. To carry out this second movement we first place the patient in the position shown with full lines in FIGS. 3 and 4, i.e. femur raised at an angle of 60° from the horizontal plane, and the tibia at a right angle to this femur. Then, while keeping the femur stationary, we pivot the tibia 28 around its main axis and plane 36, at the dimension of angle $\gamma$ of about 15°. This rotation movement of the tibia around its axis and plane is done by exercising a continuous pressure on the extremity of the foot 32, next to the ankle 30, in the direction of the knee 26. This second movement is most optimally practiced for 5 to 50 repetitions, back and forth, although more repetitions may be performed.

During this second movement, we select 50 successive positions of the appendicular skeleton, and use the transmitter, receiver and the processor to collect approximately 300 data points for the position and orientation of the marker 34, although more or fewer values may be obtained and function with the invention. For the embodiment described here, the entire sequence, including the first and second movements, results in approximately 1,200 known data points, or values, collected which correspond to three Cartesian coordinates and three polar coordinates of the marker at the reference point of the locator.

During the sequence, the trunk of the patient must remain relatively immobile within the point of reference of the locator. Light movements of less than 2 mm and rotations of less than 1° are, however, acceptable as long as their occurrences can be deemed as random.

Seven unknowns are consistent for the 200 samples taken throughout the sequence. These are, first of all, the three Cartesian coordinates of the pivot center of the hip, at the reference point of the locator of the three Cartesian coordinates of the pivot center of the knee articulation, at the actual reference point of the marker, as well as distance D separating these two pivot centers.

For j varying from 1 to 200, corresponding to the number of sample positions, we note $T_{ld}$ (j) of the homogeneous matrix known to have been taken from the three Cartesian coordinates and the three polar coordinates of the distal marker (d) measured for each sampling at the point of reference of the localizer (1).

We also note the $P_{di}$ position, i.e. the three Cartesian coordinates at the distal point of reference (d) of the intermediary articulation (i).

We also note the $P_{lp}$ position, i.e. the three Cartesian coordinates at the point of reference of the locator (1) of the pivot center of the proximal articulation (p).

Finally, we note the $P_{li}$ position, i.e. the three Cartesian coordinates at the point of reference of the locator (1) of the pivot center of the intermediary articulation (i).

By definition, the distance D separating the two pivot centers, proximal and intermediary, respectively, corresponds to the standard of the vector shaped by these centers. We can, therefore, note:

$$D = \ldots P_{li} - P_{lp}$$

$P_{lp}$ is an unknown constant during the 200 samples, which is not the case of $P_{li}$. But, by definition, we have $P_{li} = T_{ld} \cdot P_{di}$. However, $T_{ld}$ is known, and $P_{di}$ does not vary for each of the 200 positions.

We therefore have, for l=1 to 200

$$(T_{ld}(j) \cdot P_{di} - P_{lp}) = D$$

This leads to obtaining a system of 200 equations with 7 unknowns, which is highly linear and, therefore, does not allow, a priori, solution to be obtained. We, therefore, reformulate this system of equations by adding, for each one of them, either a j included between 1 and 200, or a secondary unknown called εj corresponding to an error term. We then obtain a system of 200 equations with 207 unknowns.

This system allows for an infinite number of solutions; the invention uses the one for which the sum of the squares of the εj error values is minimal. This solution is obtained, for example, by means of a classical-type minimizing algorithm for the smallest squares. We can, for example, use the commonly known LEVENBERG-MARQUARDT algorithm as well as an algorithm applying a gradient descent at a regular pace, or any other suitable algorithm now known or developed in the future.

For the embodiment described here, the use of such a least squares algorithm is preferable. However, it is also possible to solve the system of 200 equations with 7 unknowns without using an error value. In this case, we cut these 200 equations into as many sub-systems with 7 equations, so as to form a partition of 7-equation sub-systems with 7 unknowns, each one allowing a partial solution. We then obtain a number of partial solutions corresponding to the number of the partition sub-system. We then keep a final calculated solution, i.e. by arithmetic averages of the partial solutions. It is anticipated that the method of the invention will generate data which may be analyzed by any suitable commercially available program.

Once the Cartesian coordinates of the pivot centers of the hip and knee articulations are established, the computer determines the axis connecting these pivot centers. The surgeon then proceeds with cutting the femur at a 90° angle from this axis.

The invention has been described as a sequence which prompts a first movement generating three different rotations, then a second movement generating a unique rotation, for a total of four rotations. Each of the 150 positions sampled thus allows to obtain data regarding the three different rotations.

It is also possible to prompt a single movement during which the four rotations mentioned above are activated simultaneously. In this case, a smaller number of sampled positions shall be required, given that each position reveals the four simultaneous positions.

It is also possible to move the patient's appendicular skeleton in a sequence prompting three, even four successive movements, each involving one or two rotations of either bone segment around the corresponding articulation. In this case, if we wish to reach the same degree of precision as in the example described above, it is necessary to proceed with a higher number of samples than in that example.

In the described embodiment, for example, we use an optical-type marker. However, we can use any other marker, such as a magnetic or inertial marker combined with a tracking device which reports the position and orientation of this marker at a determined point of reference.

It is also possible to determine the pivot centers of the elbow and shoulder articulations, by moving the upper appendicular skeleton in accordance with a sequence involving at least two rotations of the humerus, and at least two rotations of the radius.

The procedure in accordance with the invention is preferable to traditional techniques, as it involves just one marker. Moreover, given the nature of the distal bone segment to which the marker is attached, it is not necessary to use screws. Gluing or attaching the marker on this bone segment by means of an elastic band has been found to be sufficient.

The sequence making use of two successive movements involving three different rotations, respectively, and then a sole rotation, is preferable as long as it is simple to undertaken and provides sufficient data to avoid a high number of samples.

It is understood that for example purposes a single representative embodiment is described above, although the invention may be used with many other embodiments, including all appendicular articulations. It should be understood that various changes and modifications to the embodiment described herein will be apparent to those skilled in the art. Such changes and modifications can be made without departing from the spirit and scope of the present invention and without diminishing its attendant advantages. It is therefore intended that such changes and modifications be within the scope of the claims.

I claim:

1. A system for determining pivot centers for proximal and intermediary articulations of an appendicular skeleton, the proximal articulation generally fixed in space, the system comprising:
   a) means for affixing a single marker to a distal bone segment, wherein the marker is affixed between an intermediary articulation and a distal articulation;
   b) means for moving a portion of the appendicular skeleton in accordance with a sequence involving at least one movement, said movement having at least one rotation of a bone segment around the corresponding articulation;
   c) means for collecting data points correlating to the position and orientation of the marker on a continuous basis relative to a predetermined point of reference;
   d) means for selecting a number of skeletal positions during the sequence using the collected data points;
   e) means for assigning a value to each posture representing the position and orientation of the marker in the predetermined point of reference; and
   f) means for determining the coordinates of the rotational centers of the proximal and intermediary articulations using the assigned values.

2. The system of claim 1 wherein the sequence involves:
   a) a first movement having at least first, second and third rotations of a proximal bone segment around the proximal articulation along the first and second axes in orientation orthogonal to each other; and
   b) a second movement having at least a fourth rotation of the distal bone segment around the intermediary articulation, along the third and fourth axes in orientations orthogonal to each other.

3. The system in accordance with claim 2 wherein the first movement involves a pedaling of the appendicular skeleton combined with a rotation of the skeleton around the axial axis and plane of the articulation, wherein the angle formed between the first bone in a raised position and the axial axis and plane of the articulation varies between about 40° and about 60°, wherein the angle formed between the main axis and plane of the second bone in an inclined position and the main axis and plane of the first long bone varies between about 20° and about 120°, and wherein the angle formed between the first bone and the axial axis and plane of the articulation varies between about −10° and about 20°.

4. The system in accordance with claim 2 wherein the first movement results in the rotations of the first bone around the frontal axis and sagittal axis of the first articulation, and the rotation of the second bone around the sagittal axis of the second articulation.

5. The first movement in accordance with claim 2 wherein a locator is used to find the position and orientation of the marker.

6. The system of claim 2 wherein the first movement creates about 900 data points.

7. The second movement of claim 2 wherein the first bone is placed in a stationary raised position, wherein the angle formed between the first bone and the horizontal plane is about 60°, wherein the second bone is positioned at an angle of about 90° in relation to the first bone, and wherein the second bone is pivoted about its main axis at a dimension of an angle of about 15°.

8. The system of claim 2 wherein the second movement creates about 300 data points.

9. The system of claim 2 wherein the first movement subjects the proximal or intermediary articulation to at least one helical revolution.

10. The movement of claim 9 wherein the number of helical revolutions is between about five and about fifty.

11. The marker of claim 1 comprising:
   a) at least one signal transmitting means;
   b) at least one receiving means connected to the transmitting means, wherein the receiving means is adapted to receive signals from the transmitting means; and
   c) at least one processing device connected to the receiving means.

12. The marker of claim 11 wherein the signal transmitting means is an infrared diode.

13. The marker of claim 11 wherein the receiving means includes a camera.

14. The system of claim 1 wherein the affixing means is selected from a group consisting of glue, at least one elastic band and at least one screw.

15. The system of claim 1 wherein the affixing means does not include screws.

16. The system of claim 1 wherein the sequence involves one movement, said one movement having four rotations activated simultaneously.

17. The system of claim 1 wherein the sequence involves three movements.

18. The system of claim 1 wherein the sequence involves four movements.

19. A method for determining pivot centers for proximal and intermediary articulations of an appendicular skeleton, the proximal articulation generally fixed in space, comprising the steps of:
   a) affixing a single marker to a distal bone segment;
   b) moving a portion of the appendicular skeleton in accordance with a sequence involving at least one movement, said movement having at least one rotation of a bone segment around the corresponding articulation;
   c) collecting data points correlating to the position and orientation of the marker on a continuous basis relative to a predetermined point of reference;
   d) selecting a number of skeletal positions during the sequence using the collected data points;
   e) assigning a value to each posture representing the position and orientation of the marker in the predetermined point of reference; and
   f) determining the coordinates of the rotational centers of the proximal and intermediary articulations using the assigned values.

20. The method of claim 19 wherein the sequence involves one movement, said one movement having four rotations activated simultaneously.

21. The method of claim 19 wherein the sequence involves three movements.

22. The method of claim 19 wherein the sequence involves four movements.

* * * * *

UNITED STATES PATENT AND TRADEMARK OFFICE
CERTIFICATE OF CORRECTION

PATENT NO. : 6,692,447 B1  Page 1 of 1
DATED : February 17, 2004
INVENTOR(S) : Picard, Frederic It is certified that error appears in the above-identified patent and that said Letters Patent is hereby corrected as shown below:

Column 5,
Line 40, change "y" to -- $\gamma$ -- .

Column 6,
Line 3, change "$\gamma$" to -- $\zeta$ --.

Signed and Sealed this

Sixteenth Day of November, 2004

JON W. DUDAS
*Director of the United States Patent and Trademark Office*